United States Patent [19]

Kuehn et al.

[11] Patent Number: 5,142,736
[45] Date of Patent: Sep. 1, 1992

[54] DISPOSABLE SLEEVE FOR COVERING HANDLES OF DENTIST'S LIGHTS AND METHOD OF USING THE SAME

[75] Inventors: Paul Kuehn, Eau Claire, Wis.; Thomas A. Lansing, Pine Springs, Minn.

[73] Assignee: Pinnacle Products, Inc., Eau Claire, Wis.

[21] Appl. No.: 585,490

[22] Filed: Sep. 20, 1990

[51] Int. Cl.⁵ .............................................. G05G 1/00
[52] U.S. Cl. ........................... 16/111 R; 16/DIG. 12; 362/804; 74/558.5
[58] Field of Search ............ 16/110 R, 111 R, 114 R, 16/DIG. 12, DIG. 30, DIG. 2; 206/223, 320, 439; 150/155, 161, 165, 160; 362/804, 109, 399; 74/558.5; 433/116; 118/504, 505

[56] References Cited

U.S. PATENT DOCUMENTS

| 4,777,574 | 10/1988 | Eisner | 362/804 |
| 4,795,669 | 1/1989 | Bowskill et al. | 16/114 R |
| 4,844,252 | 7/1989 | Barron et al. | 16/111 R |
| 4,975,826 | 12/1990 | Bell | 362/804 |
| 4,976,616 | 12/1990 | Eisner | 150/155 |

OTHER PUBLICATIONS

Ash/Dentsply "Disposa Shield", shield for light handle T-Bar for dentist's lights.

Primary Examiner—Robert L. Spruill
Assistant Examiner—Donald M. Gurley
Attorney, Agent, or Firm—Foley & Lardner

[57] ABSTRACT

A protective sleeve for covering the handles of a dentist's light is formed of two flexible plastic panels joined at four edges and having an aperture cut therein to allow access to the interior of the sleeve. The T-shaped handle of the light is inserted into the aperture, which is preferably elliptical in shape, and the sleeve pulled onto the handle. The sleeve is pulled off the handle after completion of a procedure on a patient and a new sleeve is put on before treatment of the next patient, thus avoiding possible transmission of disease from one patient to another from contact with the light handle.

7 Claims, 2 Drawing Sheets 5,142,736

DISPOSABLE SLEEVE FOR COVERING HANDLES OF DENTIST'S LIGHTS AND METHOD OF USING THE SAME

FIELD OF THE INVENTION

This invention relates generally to protective covers used for preventing the spread of infection and particularly to coverings for dental equipment such as dentist's lights.

BACKGROUND OF THE INVENTION

In the course of a dentist's work on a patient, he touches the T-style handles of lights that are used to focus on a patient's teeth. Every time he touches these light handles there is a concern that bioburden may be spread from the patient onto the light handles. When the dentist begins working with another patient, the possibility of cross-contamination from the previous patient arises, since the dentist will once again touch the light handles in focusing the light on the new patient. Parts of other equipment, such as x-ray exposure switches, may also be contacted by the dentist or hygienist during dental procedures.

SUMMARY OF THE INVENTION

The present invention provides an economical method of minimizing staff and patient contact with infectious materials when a dentist performs procedures on a patient. This object is attained according to the present invention in a disposable plastic sleeve which is formed to cover a T-style light handle attached to the light adjusted by the dentist in performing work on patients. The unique design of the plastic sleeve allows for easy placement over the light handle and total coverage of the light handle. The plastic sleeve is sealed on all four sides except for a small, preferably elliptical aperture in the center of one of the sides. The aperture is just big enough to allow one to easily insert the light handle into the plastic sleeve, yet is small enough to prevent the plastic sleeve from easily slipping off the light handle. The plastic sleeve's complete coverage of the light handle prevents the dentist from directly touching any part of the handle. By changing the plastic sleeves after each patient, the possibility of cross-contamination between patients is greatly reduced. Not only is the protective plastic sleeve an inexpensive means for reducing cross-contamination, but it also gives the dentist's workplace a neat appearance by eliminating the need for less attractive infection control methods like plastic wrap and aluminum foil.

Further objects, features and advantages of the invention will be apparent from the following detailed description when taken in conjunction with the accompanying drawings.

DETAILED DESCRIPTION OF THE INVENTION

Figure 1:
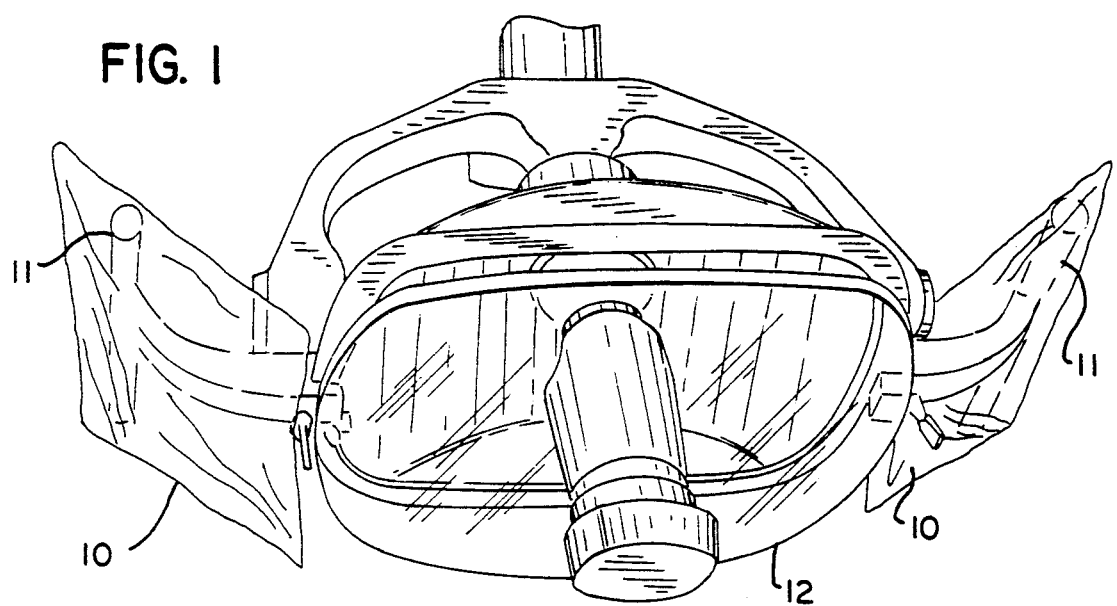
FIG. 1 is an illustrative perspective view of a dentist's light with the protective sleeves of the present invention covering the handles of the light.

With reference to the drawings, a protective plastic sleeve 10 of the present invention is illustratively shown in FIG. 1 in place on each of the handles 11 of a dentist's light 12. The sleeves 11 completely cover the T-end of the handles in the region of the handles that are grasped by a dentist to move or adjust the light 12.

Figure 2:
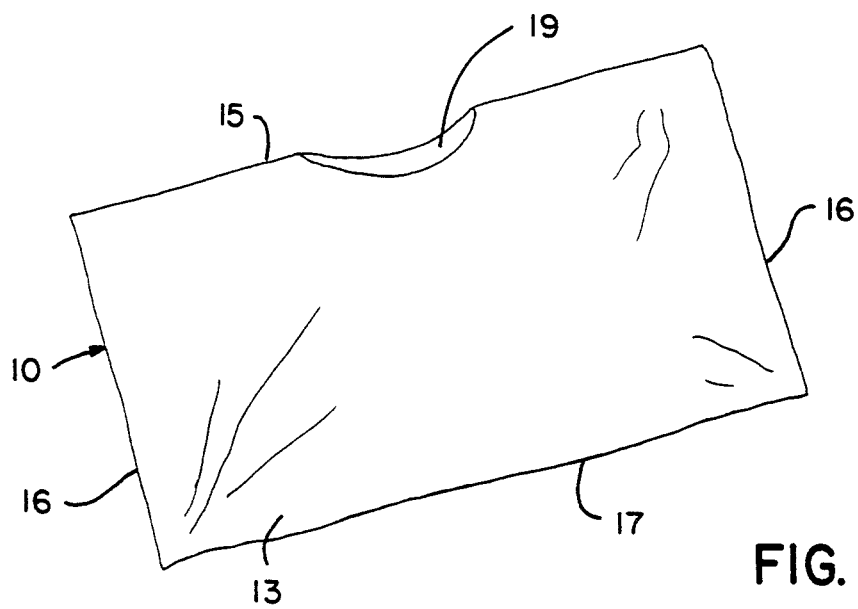
FIG. 2 illustrates a protective plastic sleeve in accordance with the invention.

The protective sleeve 10, as shown in more detail in FIG. 2, is preferably rectangular or square in shape, has two flat side panels 13 which lie flat upon one another when the sleeve is stored, and a top edge 15, two side edges 16, and a bottom edge 17. The side panel 13 are joined at the edges 15, 16 and 17 to form an enclosed volume except for an aperture 19 which extends part way across the width of the sleeve, preferably at the top edge 15. The sleeve 10 is preferably formed from a tube of flexible polyethylene film, or other suitable flexible plastic film, which is cut into sections of the desired length of the sleeve. Thus, the panels 13 are formed integrally together, with crease lines defining the top and bottom edges 15 and 17. The open ends of the tubular sections may then be heat sealed to define, for example, the side edges 16, with the top edge 15 and bottom edge 17 formed as the sealed tube is flattened to a rectangular shape. Preferably, the aperture 19 is formed by die cutting the flattened tube to cut out small section or notches of the adjacent panels 13, such as in the elliptical cut illustrated in FIG. 3. The cut to define the aperture 19 may desirably be done while the tube section is flattened and before the side edges 16 are heat sealed. The aperture could also be formed in a different shape, e.g., a "V" shape, with the requisite of the aperture being that it is narrower across than the T-end of the handles 11 so that the sleeve does not fall off the handle, but wide enough so that the handle can be inserted into the sleeve without undue difficulty, in the manner described below.

Figure 3:
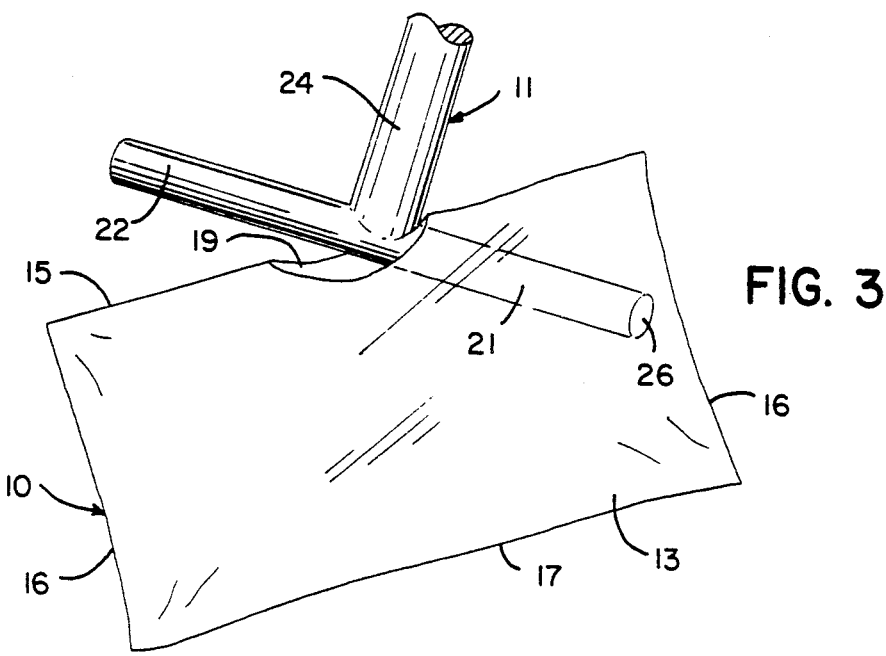
FIG. 3 illustrates a light handle partially inserted into a plastic sleeve in accordance with this invention, where one arm of the light handle is completely enclosed by the sleeve and the other arm is still outside of the sleeve.
Figure 4:
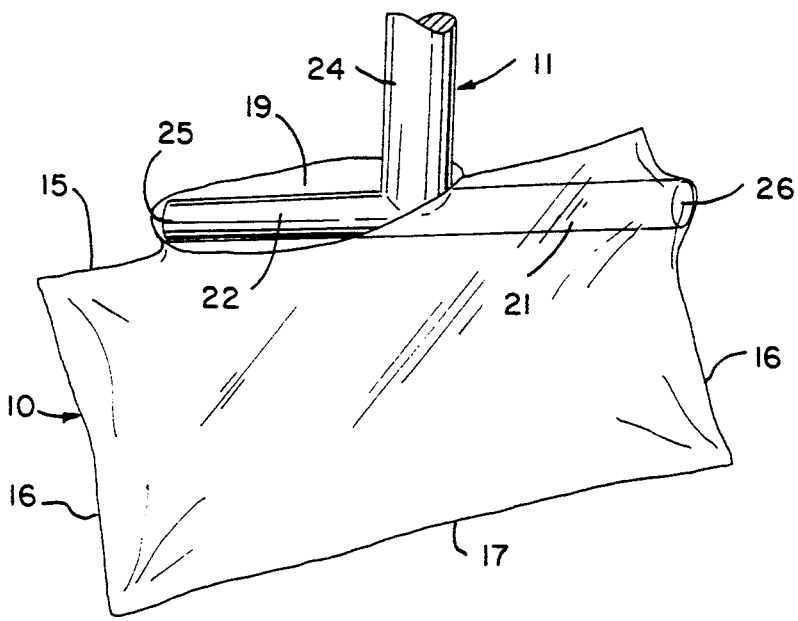
FIG. 4 illustrates a light handle partially inserted into a plastic sleeve in accordance with this invention, wherein one arm of the light handle is completely enclosed by the sleeve and the aperture of the sleeve is being stretched around the other arm.
Figure 5:
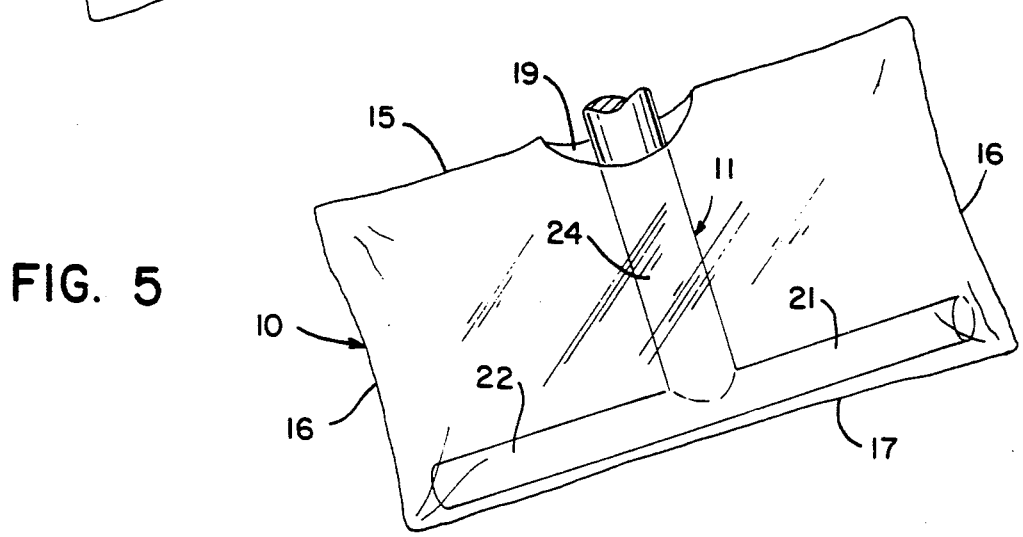
FIG. 5 illustrates a light handle completely enclosed by a protective sleeve.

FIGS. 3 through 5 depict the steps involved in covering a light handle with the protective sleeve 10. FIG. 3 shows the initial step of covering the handle in which a first arm 21 of the light handle 11 is completely enclosed by the plastic sleeve 10, while the second arm 22 remains outside of the sleeve 10. FIG. 4 shows the next step in which the first arm 21 of the light handle 11 is completely enclosed by the sleeve 10 and the second arm 22 is partially inserted into the elliptical aperture 19, the aperture 19 being stretched around the end 25 of the arm 22 of the light handle. FIG. 5 shows the last step in which both arms 21 and 22 and the stem 24 of the light handle 11 are completely covered by the sleeve 10.

Virtually any set of dimensions of the sleeve 10 can be utilized which allow for total coverage of the light handle 11 while ensuring that the sleeve does not slip off the handle. The most advantageous dimensions, however, are those that are just large enough to allow the sleeve 10 to completely cover the light handle 11 without being stretched when the handle 11 is fully inserted as shown in FIG. 5. In the preferred plastic sleeve 10, the length of the edges 15 and 17 is about 5¾ inches to 6 inches to allow both arms 21 and 22 of a standard light handle to fit snugly in the sleeve 10 without excessively stretching the sleeve. The length of the edge 16 is preferably about 4 inches so that the sleeve 10 completely encloses the stem 24 of the light handle 11.

The aperture 19 should be big enough to allow the light handle 11 to be inserted into the plastic sleeve 19 without tearing the sleeve 10, yet the aperture 19 should be small enough to prevent easy removal of the sleeve 10 from the light handle 11 once the sleeve completely covers the light handle. The aperture 19 should be a little bigger than the end of the arms of the light handle so that the first arm (21 in FIG. 2) easily slides through the aperture 19. In the preferred sleeve 10, the aperture 19 is made from an elliptical cut at the center of the edge 15 of the sleeve, where the crease forming the edge 15 of the sleeve lies along the major axis of the elliptical aperture 19. Preferably, the diameter (major axis) of the elliptical aperture 19 measured along the crease of the edge 15 is about 1½ inches to best accommodate a standard size light handle. The size of the aperture combined with the somewhat stretchable plastic, e.g., polyethylene, making up the sleeve 10 allows a user to stretch the aperture as shown in FIG. 4 without tearing the sleeve in the course of inserting the light handle 19 into the sleeve 4.

While FIGS. 2 through 5 illustrate the aperture 19 as made from a half elliptical cut into each of the panels 13 at the edge 15 of the sleeve, adjacent to one another along the edge, it is readily apparent that differently shaped apertures would also give the light handle 11 access to the interior of the sleeve. For example, a slit or rectangular cut in the center of the edge 15 may be utilized. The elliptical aperture 19 is preferable over these other aperture shapes because the elliptical cut reduces the possibility that the plastic sleeve 10 will tear when the elliptical aperture 19 is stretched prior to inserting the second arm 22 of the light handle 11 in the manner illustrated in FIG. 4. The elliptical cut distributes the stress created by stretching the elliptical aperture 19 more equally around the perimeter of the aperture 19 than would be the case for a slit or rectangular aperture. The stress on the sleeve created by stretching a slit or rectangular aperture will be concentrated on certain parts of the sleeve. Therefore, the sleeve is more likely to tear when stretched where it has an aperture created by a slit or rectangular cut in the sleeve 10. For a slit, the tear would likely occur along the line of the slit because most of the stress exerted by stretching would be concentrated along this line; for a rectangular or V-shaped cut, the tear would likely begin at one of the vertices or corners of the rectangle. For a standard light handle for a dentist's lamp, an elliptical aperture about 1-3/16 inches in length on its long axis provides both ready placement of the sleeve and good retention of the sleeve when in place on the handle.

From the above description, many variations in the described protective sleeve of this invention will be apparent to those skilled in the art. It is understood that the invention is not limited to the embodiments set forth herein as illustrative but embraces such modified forms thereof as come within the scope of the following claims.

What is claimed is:

1. A protective sleeve adapted to cover the handle of a dentist's light, comprising:
   two flexible flat plastic film panels joined together at four edges to enclose an interior and a notch in the panels at a central part of the panels together defining an aperture in the sleeve and adapted in size and shape to admit a light handle of a dentist's light therethrough, the aperture formed along one edge part way across the width of the sleeve at the center of the edge.

2. The protective sleeve of claim 1 wherein the two panels are formed integrally together and two edges are formed as crease lines and the other two edges are heat sealed together, and wherein the aperture is formed in one of the edges formed as a crease line.

3. The protective sleeve of claim 2 wherein the panels of the sleeve are formed of flexible polyethylene film.

4. The protective sleeve of claim 1 wherein the aperture is formed as adjacent half elliptical notches in the two panels at one edge defining the aperture of elliptical shape.

5. The protective sleeve of claim 4 wherein a long axis of the elliptical aperture lies along the length of the edge at which the aperture is located.

6. The protective sleeve of claim 5 wherein the long axis of the elliptical aperture is about 1-3/16 inches long.

7. The protective sleeve of claim 1 wherein the panels have edges which are from about 4 to about 6 inches long.

* * * * *